United States Patent [19]
Fischer

[11] Patent Number: 6,010,683
[45] Date of Patent: Jan. 4, 2000

[54] COMPOSITIONS AND METHODS FOR REDUCING THE QUANTITY BUT NOT THE CONCENTRATION OF ACTIVE INGREDIENTS DELIVERED BY A DENTIFRICE

[75] Inventor: Dan E. Fischer, Sandy, Utah

[73] Assignee: Ultradent Products, Inc., South Jordan, Utah

[21] Appl. No.: 09/181,103

[22] Filed: Oct. 28, 1998

Related U.S. Application Data

[63] Continuation-in-part of application No. 08/964,502, Nov. 5, 1997, abandoned.

[51] Int. Cl.⁷ ............................... A61K 7/16; A61K 7/18
[52] U.S. Cl. ............................................. 424/52; 424/49
[58] Field of Search ................................... 424/49–58

[56] References Cited

U.S. PATENT DOCUMENTS

| | | | |
|---|---|---|---|
| 2,968,628 | 1/1961 | Reed | 252/305 |
| 2,995,521 | 8/1961 | Estignard | 252/90 |
| 3,011,950 | 12/1961 | Mehaffey | 167/85 |
| 3,105,612 | 10/1963 | Krasnoff et al. | 222/78 |
| 3,422,993 | 1/1969 | Boehm et al. | 222/190 |
| 3,694,546 | 9/1972 | Roth et al. | 424/45 |
| 3,707,771 | 1/1973 | Guerra | 32/19 |
| 3,709,437 | 1/1973 | Wright | 239/343 |
| 3,791,098 | 2/1974 | Webster | 53/30 |
| 3,858,764 | 1/1975 | Watson | 222/399 |
| 3,937,235 | 2/1976 | Broughton | 132/84 B |
| 3,937,364 | 2/1976 | Wright | 222/190 |
| 3,946,108 | 3/1976 | Tomlinson et al. | 424/49 |
| 3,947,567 | 3/1976 | Berg et al. | 424/45 |
| 3,955,942 | 5/1976 | Cordon et al. | 51/295 |
| 3,964,649 | 6/1976 | Alexander | 222/399 |
| 3,985,668 | 10/1976 | Hartman | 252/99 |
| 3,988,433 | 10/1976 | Benedict | 424/53 |
| 4,018,364 | 4/1977 | Wright | 222/190 |
| 4,022,351 | 5/1977 | Wright | 222/145 |
| 4,027,789 | 6/1977 | Dickey | 222/190 |
| 4,047,645 | 9/1977 | Caliendo | 222/386.5 |
| 4,051,056 | 9/1977 | Hartman | 252/99 |
| 4,066,745 | 1/1978 | Tomlinson et al. | 424/49 |
| 4,093,123 | 6/1978 | Maran | 239/322 |
| 4,102,992 | 7/1978 | Davis | 424/49 |
| 4,111,713 | 9/1978 | Beck | 106/288 |
| 4,143,126 | 3/1979 | Gaffar | 424/49 |
| 4,184,615 | 1/1980 | Wright | 222/190 |
| 4,588,582 | 5/1986 | Motarjemi | 424/49 |
| 4,651,905 | 3/1987 | Hayes | 222/394 |
| 4,770,634 | 9/1988 | Pellico | 424/52 |
| 4,834,969 | 5/1989 | Grollier | 424/49 |
| 4,836,422 | 6/1989 | Rosenberg | 222/190 |
| 4,969,577 | 11/1990 | Werding | 222/94 |

(List continued on next page.)

FOREIGN PATENT DOCUMENTS

| | | |
|---|---|---|
| 1319875 | 7/1993 | Canada . |
| 82/03975 | 11/1982 | WIPO . |

*Primary Examiner*—Shep K. Rose
*Attorney, Agent, or Firm*—Workman, Nydegger, Seeley

[57] ABSTRACT

Toothpaste and other dentifrices formulated to include a volume increasing agent (density reducing agent) in order to significantly increase the volume of the toothpaste at the time it is dispensed onto a toothbrush. The inventive dental compositions preferably include a substantial quantity of entrained air or other gas in order to reduce the density, and hence the weight, of toothpaste actually placed within a person's mouth. The result is a reduction in the amount of active ingredients introduced into a person's mouth that might be ingested. The entrained air or other gas can also increase the availability of the active ingredient since the foamed composition increases the dispersibility of the active ingredients within saliva. The net effect is that a person decreases the actual amount of toothpaste without decreasing the volume, or visual amount, of toothpaste dispensed on the toothbrush. The density-reduction effect can be augmented using a low density filler in addition to, or instead of, entrained gas. The inventive dentifrices might be pre-foamed with a storage container or formulated to foam in situ when dispensed from the storage container.

43 Claims, 1 Drawing Sheet

U.S. PATENT DOCUMENTS

| | | | |
|---|---|---|---|
| 4,995,533 | 2/1991 | Vandoninck | 222/54 |
| 5,048,750 | 9/1991 | Tobler | 222/189 |
| 5,071,637 | 12/1991 | Pellico | 424/45 |
| 5,073,363 | 12/1991 | Pellico | 424/49 |
| 5,090,595 | 2/1992 | Vandoninck | 222/54 |
| 5,110,583 | 5/1992 | Sampathkumar | 242/48 |
| 5,124,143 | 6/1992 | Müllemann et al. | 424/49 |
| 5,230,648 | 7/1993 | Kelley et al. | 446/74 |
| 5,266,304 | 11/1993 | Baffelli et al. | 424/49 |
| 5,407,287 | 4/1995 | Braun et al. | 401/176 |
| 5,597,553 | 1/1997 | Baffelli et al. | 424/49 |
| 5,665,332 | 9/1997 | Mundschenk et al. | 424/49 |
| 5,736,158 | 4/1998 | Quast | 424/464 |
| 5,824,289 | 10/1998 | Stoltz | 424/45 |

COMPOSITIONS AND METHODS FOR REDUCING THE QUANTITY BUT NOT THE CONCENTRATION OF ACTIVE INGREDIENTS DELIVERED BY A DENTIFRICE

RELATED APPLICATIONS

This application is a continuation-in-part of copending U.S. application Ser. No. 08/964,502, filed Nov. 5, 1997 (abandoned). For purposes of disclosure, the foregoing application is incorporated herein by specific reference.

BACKGROUND OF THE INVENTION

1. The Field of the Invention

The present invention is in the field of oral dentifrices, particularly in the field of toothpastes. More particularly, the present invention relates to toothpastes that are foamed and stabilized in order to reduce the overall mass of toothpaste that is dispensed during use and increase the rate of dispersion of the toothpaste onto the person's teeth. Such dentifrices deliver a lower quantity of active ingredients while maintaining required concentrations.

2. The Relevant Technology

Toothpastes and other dentifrices are widely used in America and throughout the world to provide good oral hygiene, to prevent tooth decay, remove stains and to treat or minimize other problems associated with oral hygiene, such as gum disease and foul breath odor. Toothpastes typically include an inert carrier gel or paste, abrasive agents for removing plaque and other impurities found on a person's teeth, decay preventing medicaments, such as fluorides, flavorants, surfactants, detergents, and other additives to provide a desired consistency and cleansing or medicinal activity. While many ingredients may be added or eliminated according to fads or perceived specialized needs, such as baking soda or tartar removing agents, modern toothpastes almost uniformly include fluoride in one form or another.

Fluoride has been medically proven to aid in the prevention of tooth decay. Typically, tooth decay causing agents generally comprise acids formed by bacterial breakdown of sugars in a person's mouth. Enamel treated with fluoride is much more resistant to such acidic attack compared to enamel that has not been treated with fluoride.

Nevertheless, there are some problems associated with the careless use of fluoride. While topical administration of fluoride to teeth provides reduced tooth decay, fluorides can be harmful if ingested in large enough amounts. Ingesting too much fluoride can lead to fluorosis and even death in some cases. Even if sublethal doses of fluoride are ingested, a person with fluorosis will often develop brown, mottled enamel and/or bone dyscrasia and other abnormalities. Even lower levels of fluoride ingestion can cause significant tooth discoloration. In higher amounts, the fluoride can affect the structural formation of teeth and cause inappropriate development, particularly in children.

While fluorosis can affect persons of any age, it is particularly pronounced in children. This is because children are much smaller and have far less body mass compared to adults. In addition, their bodies are in the development stage so that health problems have a more permanent and long-term effect. Therefore, a quantity of fluoride that is safe when ingested by an adult might be harmful if ingested by a child.

Moreover, because children are generally resistant to certain hygienic practices, including brushing their teeth on a regular basis, toothpaste manufacturers have deliberately developed toothpaste that taste good to encourage brushing. While this might have the beneficial effect of encouraging more brushing by children, it has the negative side effect of enticing children to swallow the toothpaste while they brush. Depending on the taste, children may intentionally or unintentionally shallow substantial amounts of toothpaste. Moreover, children generally do not understand that it is not proper to swallow toothpaste and might swallow large amounts even though many toothpastes for children include a warning label against ingestion of the product. Much of the problem stems from the tendency of children to apply too much toothpaste onto the brush.

Because of the known dangers associated with ingesting high levels of fluoride, toothpaste manufacturers generally recommend that children use only a pea-size quantity of toothpaste on the brush. A "pea-size" amount is typically about ⅓ the amount of toothpaste needed to fully cover an adult-sized toothbrush, as seen on advertisements generally. While such warnings are certainly proper, they are often not understood and ignored by both adults and children alike. In general, children simply do not understand that fluoride, while beneficial in very low doses, can be a poison at higher levels.

In real-life situations, most humans including children will lay a solid strip of toothpaste across the entire length of the toothbrush bristles. This is not surprising since we are all familiar with the ubiquitous television and print advertisements showing an inviting and generous quantity of toothpaste that runs the length of the toothbrush bristles, and even curls artistically and invitingly up and around on the end to form a solid strip across the length of the toothbrush with a "curly-Q" on one end. It is obviously in the toothpaste manufacturer's best interest to encourage the use of larger quantities of toothpaste, even though wasteful, in order to cause faster toothpaste depletion and more subsequent sales.

Because of this reality, the unfortunate result is that children have been found to develop fluorosis, which causes brown, mottled enamel. In addition, even more moderate doses of fluoride can create discoloration, affect structural formation of teeth, and cause diseased teeth and bones. It is possible that the dangers of fluoride ingestion by children might actually outweigh the benefits of fluoride in fighting tooth decay, at least in some cases.

In addition to fluoride, toothpastes can include other ingredients which, while beneficial when applied topically in the mouth, might have unwanted side effects if ingested. Other ingredients in toothpaste that should not be ingested include surfactants, agents used to fight gum disease, tartar removal agents, bleachants, and other cleansing or disinfecting agents that are intended for topical application only.

In light of the foregoing, what are needed are compositions and methods for manufacturing toothpastes and other dentifrices which reduced the level of fluoride and other active ingredients that might be ingested by adults or children while still providing their beneficial effects.

It would be an additional improvement in the art to provide compositions and methods for manufacturing toothpastes and other dentifrices that provided the desired concentration of active fluoride and other dental agents while reducing the amount delivered by the dentifrices.

Moreover, it would be a marked improvement in the art to provide compositions and methods for manufacturing toothpastes and other dentifrices that yielded compositions having an increased rate of dispersion of the fluoride and/or other active ingredients compared to conventional toothpastes.

In particular, it would be a tremendous improvement in the art to provide compositions and methods for manufacturing toothpastes and other dentifrices that had increased dispersibility in saliva such that the active dental agent, such as fluoride, is more rapidly available to effect its beneficial activity.

Such compositions and methods for manufacturing improved toothpastes and other dentifrices are disclosed and claimed herein.

SUMMARY AND OBJECTS OF THE INVENTION

The present invention relates to compositions and methods which increase the dispersibility of the active ingredients found in toothpastes and other dentifrices while reducing the overall mass of such ingredients in order to limit the danger associated with their possible ingestion. Particularly, the present invention relates to toothpastes and other dentifrices having an increased volume-to-mass ratio in order to provide what looks and feels like a desired quantity of toothpaste, while reducing the actual amount that is delivered. This can be accomplished by incorporating substantial amounts of air or other gases or inert lightweight fillers, which shall hereinafter be referred to as a "density reducing component" or "density reducing means". They may also be referred to bulkifying agents, which add bulk and size to the dental compositions without adding substantial mass.

Besides reducing the density of the toothpaste, entrained gas has the additional benefit of increasing the dispersibility of active ingredients within the dentifrice so that they thereby have greater contact time with the person's teeth. Foamed toothpastes or other dentifrices have greatly increased solubility in saliva, which provides for greater availability and increased uptake of the active ingredients by the teeth or surrounding tissues. They also reduce the actual amount of active ingredients placed within the person's mouth, thus reducing the risk of ingesting lethal or unhealthy quantities of active dental medicaments, such as fluoride, by children and incapacitated adults.

Whereas toothpaste manufacturers provide warning labels that state that children should use only a pea-sized quantity of toothpaste on the brush, this message is in small print and is also drowned out by the more seductive and persuasive advertising campaigns showing a generous quantity of toothpaste laid out as a solid, voluptuous strip across the brush. Because it is natural for people to want more of a "good thing", people naturally waste toothpaste in spite of warning labels. Even if a manufacturer teaches the benefits of using less toothpaste and chooses not to advertise the use of greater quantities, the images provided by other manufacturers may nevertheless stick in the public's mind and overwhelm a particular manufacturer's good intentions.

In light of the foregoing, the advantage of foaming the toothpaste is that it creates the illusion of having a large quantity of toothpaste. This illusion allows persons, particularly young children, to safely use a longer strip of toothpaste across the toothbrush bristles. The inventive toothpaste will, however, contain a significant volume of entrained gas such that the overall mass of toothpaste and active ingredients dispersed therein will typically be much lower than the visual appearance. This allows a child, for example, to cover the toothbrush with a longer strip of toothpaste, while delivering a much smaller quantity of actual toothpaste, since the strip is a mixture of toothpaste and inert gas or lightweight filler.

Not only does the foam create the illusory effect of having more instead of less, the foam has the additional advantage of causing the toothpaste or other dentifrice to mix and disperse more rapidly with saliva. This causes the toothpaste to more quickly spread across the teeth and into crevices to provide faster cleaning and treatment of the teeth. Thus, foaming the toothpaste causes it to have the ability to gain proximity to tooth surfaces and crevices far more quickly than conventional toothpastes. Because most people on average brush for 60 seconds or less, it is important that the fluoride or other active ingredients are rapidly deployed over the surface of the person's teeth. Otherwise, their intended benefit may not be realized to the extent desired.

The result of entraining substantial quantities of gas within toothpaste is that it allows the formulation of toothpastes designed to have greater dispersibility, e.g., faster dispersion and availability of fluoride, more detergent action, greater anticariogenic action, more antiplaque action, and/or higher antigingivitis action in the more active foam. Hence, the foam facilitates the creation of tooth products that more effectively and rapidly deliver more dental treatment action whether or not the active ingredient(s) is more concentrated, while providing a significantly lower actual quantity or mass of the active ingredient(s) that might be harmful if ingested.

Alternatively, the desired benefits can be provided by using a toothpaste dispenser or formulation that has the ability to foam the toothpaste in situ, or just prior to use, by the person dispensing the toothpaste. For example, a container of toothpaste can be provided in conjunction with a small compartment of compressed gas that could be mixed with the toothpaste during the dispensing process in order to foam the toothpaste at the time of use. Alternatively, the toothpaste can include entrained gas but is stored under pressure. Upon dispensing, the compressed gas will expand and cause in situ foaming of the toothpaste, similar to how shaving foam behaves. The final result would essentially be the same as using pre-foamed toothpaste, but with lower initial volume.

It should be understood that virtually any toothpaste known in the art can be modified so that it includes substantial quantities of entrained air or other gas in order to create the aforementioned benefits of foamed toothpaste. Therefore, while the present application discusses certain preferred methods and/or additives that facilitate the formation of stable foamed toothpaste, it should be understood that any conventional toothpaste known in the art that incorporates substantial quantities of entrained gas or air such that a toothpaste of greatly reduced mass can be dispensed onto the user's toothbrush will be within the scope of the present invention. An example of a toothpaste composition known in the art is set forth in U.S. Pat. No. 3,988,433 to Benedict. For purposes of disclosing toothpaste compositions, the foregoing patent is incorporated herein by specific reference.

In order to manufacture a stable foamed toothpaste containing entrained air or other gas, the toothpaste composition will preferably include an appropriate foaming agent, one or more gelling or thickening agents, and an additional stabilizing agent for maintaining a stable foam. Depending on the desired level of aeration and the desired toothpaste consistency, the concentrations of thickening agent and stabilizer would generally need to be adjusted for a desired toothpaste formulation. For example, toothpastes that will include greater quantities of air or other gas will generally need to include greater concentrations of thickening or gelling agents in order to maintain a desired stiffness or consistency, since the inclusion of greater quantities of entrained gas will tend to soften or liquify toothpaste compositions that would otherwise be more stiff or gel-like if lesser quantities of air were entrained. Moreover, toothpastes that include more entrained gas will generally require greater quantities of the foam stabilizing agent.

In general, the level of gelling or thickening agent will be similar in the case where the toothpaste is aerated in situ as where it is aerated during manufacture. However, it might be possible to reduce the amount of stabilizing agent, or even eliminate it altogether, in the case where the toothpaste is aerated in situ since it will only be necessary for the foam to remain stable long enough to provide the visual benefits outlined herein prior to use, as opposed to the weeks, months, or years in the case of pre-foamed toothpastes.

In many cases, toothpastes also include surfactants such as sodium laurel sulfate that cause them to foam when mixing with saliva. This helps to more quickly dissolve the toothpaste in the saliva and increase the uptake of medicaments such as fluoride. In the present invention, providing a toothpaste that is already foamed will create a more easily dissolvable toothpaste reducing the need for added detergents. This has the benefit of reducing the potential for ingestion of detergents. While not usually toxic in most individuals, detergents can nevertheless cause some gastrointestinal discomfort. In the case where detergents are used, the pre-foamed toothpaste will further increase the solubility of the toothpaste in saliva and the associated availability and uptake of dispersed medicaments.

In order to provide the foregoing benefits of increased dispersibility and availability of dispersed medicaments within toothpastes and other dentifrices, air or other gas may be entrained within the toothpaste or other dentifrice in an amount in a range from about 10% to about 90% by volume of the toothpaste or other dentifrice, preferably greater than about 20% by volume, more preferably greater than about 30% by volume, and most preferably greater than about 50% by volume of the toothpaste or other dentifrice.

Instead of, or in addition to, incorporating substantial quantities of a gas, the inventive dentifrices may include a lightweight solid filler. The term "lightweight solid" will refer to solid fillers that are generally insoluble in the liquid components of the dentifrice and which will have a density less than about 1 g/cm$^3$, preferably less than about 0.50 g/cm$^3$, more preferably less than about 0.3 g/cm$^3$, and most preferably less than about 0.1 g/cm$^3$. Because the lightweight solids can act to displace a substantial portion of the active dentifrice without substantially reducing the concentration of the active dental agent within the active dentifrice portion, lightweight solids can behave similarly to entrained gas as described herein.

Examples of lightweight, low density solid fillers include, but are not limited to, foamed polystyrene particles, polypropylene spheres, polymeric beads, perlite, vermiculite, hollow glass spheres, lightweight expanded geologic materials, and the like. In addition to adding bulk and greatly reducing the density of the dental composition, the lower density solid filler can be selected to optionally impart an abrasive action such that it can assist the other abrasives included within the dental composition. The only limitation is that the foamed organic solid should substantially reduce the density of the toothpaste but also be safe when placed within the oral cavity of a human.

In light of the foregoing, it is an object of the present invention to provide compositions and methods for manufacturing toothpastes and other dentifrices which reduce the amount of fluoride and other active ingredients that might be ingested by adults or children while still providing their beneficial effects.

It is a further object of the present invention to provide compositions and methods for manufacturing toothpastes and other dentifrices that provide the desired concentration of active fluoride and other dental agents while reducing the amount delivered by the dentifrice.

In addition, it is an object of the present invention to provide compositions and methods to provide manufacturing toothpaste and other dentifrices that yield compositions having an increased rate of dispersion of fluoride and/or other active ingredients compared to conventional toothpastes.

It is a further object of the present invention to provide compositions and methods for manufacturing and other dentifrices that have increased solubility and dispersibility in saliva such that the active dental agent, such as fluoride, is more rapidly available to effect its beneficial action.

These and other objects and features of the present invention will become more fully apparent from the following description and appended claims, or may be learned by the practice of the invention as set forth hereinafter.

BRIEF DESCRIPTION OF THE DRAWINGS

In order that the manner in which the above-recited and other advantages and objects of the invention are obtained, a more particular description of the invention briefly described above will be rendered by reference to a specific embodiment thereof which is illustrated in the appended drawings. Understanding that these drawings depict only a typical embodiment of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

1. INTRODUCTION

Figure 1:
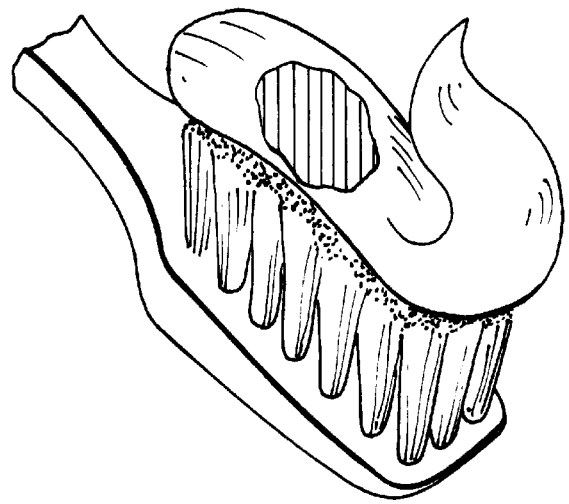
FIG. 1 is a perspective view of the end of a toothbrush having a solid strip of a conventional toothpaste and showing a breakaway section of the toothpaste.

The present invention relates to compositions and methods for creating foamed toothpastes and other dentifrices in order to reduce the density of the toothpaste, or mass per unit volume. The benefit of doing this is at least twofold. First, it allows a person to dispense what appears to be a generous, full-bodied quantity of toothpaste onto the toothbrush as desired while reducing the actual quantity or mass of toothpaste being dispensed. This, in turn, reduces the quantity of active ingredients that might accidentally be ingested. Second, it increases the dispersibility of the toothpaste or other dentifrices in saliva or other aqueous systems, which accelerates or increases the availability of the active dental agents, particularly the uptake of fluorides. In other words, the inventive dental compositions at the same time provide increased effectiveness while lowering the risk of accidental poisoning by the active ingredients.

Fluorides and other medicaments are very useful in preventing tooth decay and treating other dental or oral ailments. The active ingredients in toothpaste and other dentifrices are usually safe when applied topically to tooth surfaces and/or gums. Medicaments found in toothpastes generally have little or no utility if ingested and can be harmful or even fatal if ingested in great enough quantities. This is particularly true in the case of children, who are generally much more sensitive to toxic doses of fluoride or other medicaments, or medicaments in which the threshold level of toxicity is far less in children due to their greatly smaller size and body weight compared to adults. By way of comparison, an adult weighing six times more than a child would have to ingest roughly six times more of a toxin in order for the toxin to have the same level of harm or toxicity.

In addition, whereas an adult has already gone through the growth stage, a child is still in the early stages of bodily development, which can create a whole array of developmental problems not experienced by adults. For example, in the early developmental stages of a child's teeth, particularly when baby teeth are replaced by permanent teeth, excessive fluoride, even if ingested in non-lethal amounts, can cause severe staining and mottling of the teeth. Excessive fluoride can also cause bone dyscrasia and other abnormalities, as well as inappropriate development of the teeth in general. For this reason, there has been growing concern that children should reduce the amount of fluoride intake in order to avoid the foregoing problems.

The reduction of fluoride in children has been problematic for a number of reasons, some political rather than scientific. First, the Food and Drug Administration of the United States has mandated that, in order to make the claim that a toothpaste contains fluoride, a manufacturer must include the minimum mandated concentration of fluoride, as measured in parts per million. By law "fluoride toothpastes" must include the mandated minimum concentration of fluoride, regardless of whether the toothpaste is intended for adults or children. Therefore, toothpaste formulations for children are required by the government to have the same concentration of fluoride as adult compositions, notwithstanding the increased danger to children of such fluoride concentrations.

Instead of including lessor quantities of fluoride, the only identifiable difference between children's toothpaste and toothpastes made for adults is that children's toothpastes taste better. Some adult toothpastes often include unpleasant tasting ingredients, such as baking soda, tartar removing agents, plaque removing agents, and other medicaments. In contrast, to promote brushing children's toothpaste are often manufactured to taste as delicious as possible. Unfortunately, better tasting toothpastes may also encourage a young child to swallow the toothpaste while brushing, or worse yet, eat the toothpaste even while not brushing. As a result, children on average ingestfar more toothpaste than adults, the harm of which is further multiplied by the child's greatly reduced body weight. The potential risk is severe tooth maldevelopment, discoloration, and mottling of enamel, and in some cases, even death.

Although toothpaste manufactures now recommend that children only use a "pea-size" quantity of toothpaste on the brush, such warnings are unheeded by children who either cannot read or do not fully comprehend or appreciate the risks associated with ingesting toothpaste. Moreover, children are bombarded by television and print advertisements showing a generous, full-bodied strip of toothpaste across the entire length of the toothbrush bristles. Common experience has shown that children tend to be far more vulnerable to media campaigns than adults, and the mental impressions formed by seeing a large, full-bodied amount of toothpaste are far more powerful and persuasive than recommendations to use a pea-size quantity.

In light of this, the inventors have developed compositions and methods for manufacturing toothpastes that greatly reduce the actual quantity of fluoride or other medicaments that enter a person's mouth by way of toothpastes or other dentifrices, while giving the person the illusion of receiving a large quantity by allowing the person to dispense a full-bodied, solid strip of toothpaste across the toothbrush. Hence, a person can have the satisfaction of feeling like he or she has used a large, even wasteful, amount of toothpaste, while in reality the actual mass of toothpaste has been substantially reduced such that the person ends up using the recommended quantity.

In order to illustrate the utility of the invention, reference is now made to the drawings. FIG. 1 shows a solid, full-bodied quantity of a conventional toothpaste spread across the length of a standard adult toothbrush, with a swirled, wrap-around portion of toothpaste as a cute accent on one side. Manufacturers have conditioned the public to believe that the toothpaste depicted in FIG. 1 is the satisfying and desired amount. FIG. 1 also includes a break-away section of the toothpaste showing the interior of the toothpaste, which can be seen to be a solid mass of gel or paste with no air entrainment. In reality, the quantity of toothpaste depicted in FIG. 1 is far greater than what is necessary to actually clean the teeth and provide adequate fluoride treatment.

In fact, common experience shows that when relatively large quantities of toothpaste are used, much of it is wasted by either falling from the person's mouth into the sink or by not being adequately dispersed throughout the person's saliva. In any event, because cleansing and fluoride treatment of teeth is largely a surface reaction, any toothpaste not directly in contact with the surface of the teeth is largely wasted and should be considered excessive. Moreover, in the case of young children or mentally disabled adults, excess toothpaste may often be ingested, either accidentally or intentionally. Thus, using the amount of toothpaste depicted in FIG. 1 is not only wasteful but potentially harmful.

Figure 2:
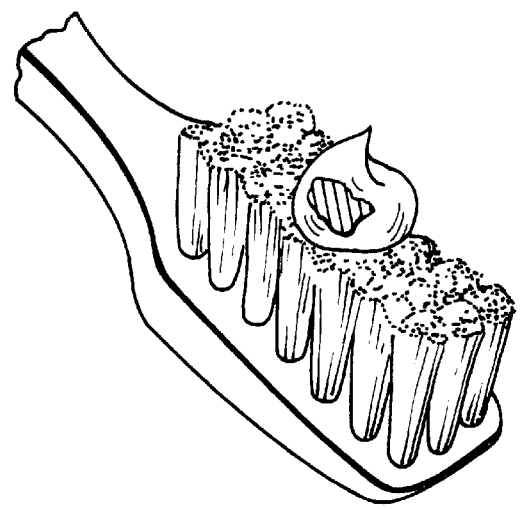
FIG. 2 is a perspective view of the end of a toothbrush having a "pea-size" amount of toothpaste.

FIG. 2 depicts a "pea-size" amount of toothpaste on the toothbrush, which is adequate for most people, not just children. Not only is this the recommended quantity for young children, it is also a realistic amount of toothpaste that will adequately cleanse an adult's teeth and provide sufficient fluoride treatment. Notwithstanding this, one has rarely if ever encountered a television or print ad showing a pea-size quantity of toothpaste on a toothbrush. The result is that people have been conditioned to feel a sense of deprivation if only a pea-size amount were used.

By way of comparison, the quantity of toothpaste required to cover a typically-sized adult toothbrush illustrated by FIG. 1 weights about 2.4 g, while the "pea-sized" amount illustrated by FIG. 2 weighs approximately 0.8 g. Thus, the pea-size amount recommended by children's toothpaste manufacturers is about ⅓ the size of a "normal amount". The amount of fluoride delivered into a person's mouth by the amount illustrated by FIG. 1 is about 0.0026 g, while the amount within the pea-sized quantity illustrated by FIG. 2 is only about 0.00088 g, which is ⅓ as much.

Figure 3:
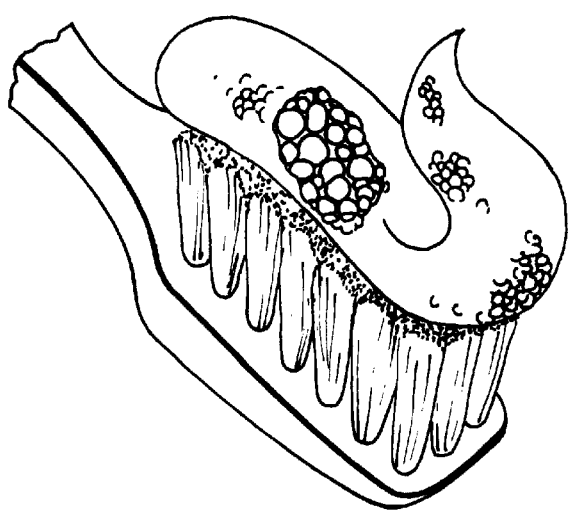
FIG. 3 is a perspective view of the end of a toothbrush having a solid strip of a foamed toothpaste of the present invention and showing a breakaway section of the toothpaste.

FIG. 3 shows a large, full-bodied strip of a low density toothpaste made according to the present invention on top of an adult tooth brush. By way of comparison, assuming that the amount of toothpaste depicted in FIG. 2 is ⅓ the size of the toothpaste depicted in FIG. 3, and also assuming that the toothpaste in FIG. 3 has only ⅓ the density of the toothpaste depicted in FIG. 2, the actual quantity or mass of the two toothpaste amounts depicted in FIGS. 2 and 3 is the same. On the other hand, the actual quantity of toothpaste depicted in FIG. 1 is three times the amount shown in FIG. 3, although they look the same.

This clearly and succinctly demonstrates the beauty of the invention: the very satisfying and generous amount of toothpaste depicted in FIG. 3 looks the same as the amount in FIG. 1 but is, in actuality, the same as the pea-size amount depicted in FIG. 2. The result is that children and adults can be, in effect, fooled into thinking they are getting a standard quantity of toothpaste while, in reality, they are being limited to the equivalent of a pea-sized amount. Moreover, because only the density has been reduced, the toothpaste of FIG. 3 can have the same concentration of fluoride as the toothpastes of FIGS. 1 and 2, thus satisfying the demands of the FDA for fluoride toothpastes. The result is that a person gets to use "more" of a fluoride toothpaste having the mandated concentration of fluoride, while actually receiving a more limited actual quantity of fluoride that might be ingested.

If the only effect of entraining air were to reduce the risk of fluorosis and other ailments that can result from ingestion of fluoride and other medicaments in toothpastes and other dentifrices, then the dental compositions of the present invention would have great utility. Nevertheless, the inventors have found that foaming the dental compositions often increases the dispersibility and, hence, the availability of the active ingredients in the dentifrice, sometimes dramatically. It is postulated that this is due to the enhanced ability of foamed toothpastes or other dentifrices to dissolve or disperse within saliva and water such that the active medicaments, such as fluoride, are more quickly dissolved into the person's saliva and then dispersed over the tooth surfaces being treated.

One possible reason for this is that foamed toothpastes having entrained air or air pockets have a greatly increased effective surface area, which greatly increases the interface area between the toothpaste and saliva or water. This, in turn, can increase the solvating action of the saliva and/or water. The result is greater availability and uptake of fluoride and other medicaments, even though the actual amount of such medicaments has been reduced as a result of providing a lower density dentifrice. The result is greater efficiency per unit mass of the active ingredient. Because most people on average brush for 60 seconds or less, it is important that the fluoride or other active ingredients be rapidly deployed over the surface of the person's teeth. Otherwise, their intended benefit may not be realized to the extent desired.

II. CONSTITUENTS WITHIN THE INVENTIVE DENTAL COMPOSITIONS

In order to manufacture foamed dentifrice compositions, the inventors have identified a number of components which aid in the formation of the inventive dentifrice and the stabilization of the air entrainment if necessary. It should be understood that virtually any toothpaste in the market or known in the art can be modified so that it includes substantial quantities of entrained air or other gas in order to create the aforementioned benefits of foamed toothpaste. Therefore, while the present application discusses certain preferred methods and/or additives that facilitate the formation of stable foamed toothpaste, it should be understood that any conventional toothpaste known in the art that incorporates substantial quantities of entrained gas or air such that a toothpaste of greatly reduced mass can be dispensed onto the user's toothbrush will be within the scope of the present invention. An example of a toothpaste composition known in the art is set forth in U.S. Pat. No. 3,988,433 to Benedict, which has heretofore been incorporated by reference for purposes of disclosure.

A. Base Composition

The portion of the dental composition exclusive of the density reducing means or density reducing component comprises the "base composition". In other words, the "base composition" is that portion of the overall dental composition besides the density reducing means. In the case where the density reducing means comprises a gas, the base composition will supply essential all of the mass or weight of the final dental composition of reduced density, since the gas provides an insignificant quantity of mass or weight. In the case where the density reducing means includes or consists of a low density solid filler, the filler will provide a much lower percentage of the mass or weight compared to the base composition. The base composition comprises one or more dental agents dispersed within a carrier. In the case of a dental composition used to clean teeth, the base composition will preferably include an abrasive to assist in cleaning the person's teeth.

1. Dental Agents

The primary dental agent found in virtually all toothpastes is fluoride, which is an anticarious compound used to prevent tooth decay. Although very beneficial if used in appropriate quantities, fluoride can become dangerous if ingested in significant quantities. Examples of fluoride compounds useful as a decay prevention agent include, but are not limited to, sodium fluoride, potassium fluoride, calcium fluoride, magnesium fluoride, sodium fluorosilicate, stannous fluoride, stannous monofluorophosphate, sodium monofluorophosphate, and copper fluoride. Each of the foregoing fluoride compounds comprises a "fluoride ion source". A more complete discussion of fluoride compounds useful in fighting cavities may be found in U.S. Pat. No. 3,535,421 to Briner et al. For purposes of disclosure, the foregoing patent is incorporated herein by specific reference.

In order to deliver an effective amount of fluoride to a person's teeth, the foamed dental compositions of the present invention will include a fluoride concentration such that the fluoride ions are included in a range from about 10 ppm to about 3500 ppm, more preferably in a range from about 850 ppm to about 1150 ppm of fluoride ions. The exact amount of fluoride will depend on the solubility and dispersibility of fluoride and also FDA guidelines for fluoride-containing toothpaste. The FDA presently requires "fluoride toothpastes" to include at least 900 ppm of available fluoride ions.

Other dental agents or medicaments that can be included instead of, or in addition to, fluoride include antimicrobial agents that can be added to fight gum and periodontal diseases and desensitizing agents. Examples of antimicrobial agents include, but are not limited to chlorhexadine, tetracycline, cetyl pyridinium chloride, benzalkonium chloride, cetyl pyridinium bromide, methylbenzoate, propylbenzoate, and peroxides. Examples of desensitizing agents include, but are not limited to, potassium nitrate, citric acid, citric acid salts, strontium chloride, and the like.

2. Carrier

In order to deliver the appropriate concentration of dental agent to the user, the dental agent should be dispersed within a flowable substance that will allow for the dental agent to be dispensed onto e.g, a toothbrush. Because any toothpaste or dentifrice known in the art can be modified to include substantial quantities of entrained air or gas, the appropriate carrier could be any substance known in the art that has been found useful as a carrier in manufacturing toothpaste and tooth gels known in the art.

The term "carrier" as used herein, is defined as one or more compatible components which dilute and deliver the dental agent in appropriate quantities in an appropriate manner. Hence, appropriate carriers may include solid, liquid, gel-like, and gaseous components. Such components should be "compatible", which means that they are capable of being used together in a foamed composition without destabilizing or otherwise adversely affecting the foamed nature of the dental composition so that it will behave in the desired manner.

Examples of components found in carriers within conventional toothpastes are set forth in U.S. Pat. No. 3,988,433 to Benedict, the disclosure of which is incorporated herein by reference. Although Benedict may not necessarily use the term "carrier" to define the components found therein, any component other than the dental agent or medicament found in the composition of Benedict may fairly be referred to as a "carrier" component.

Materials that are used as carriers may also be used for other purposes in a dentifrice composition, such as acting as a humectant, abrasive, thickener, foaming agent, surfactant, and the like. Thus, although one of the components used in a toothpaste may be identified as providing a particular function, as used herein such other components will normally be classified under the rubric of being a "carrier" so long as it in some way aids in the delivery of an appropriate concentration of fluoride or other dental agent.

Carriers typically include a water-soluble gel or other material that gives bulk to the dental composition. Typically, a thickener or gelling material is dispersed in water or other solvent such as glycerine or polyethylene glycol to yield a carrier safe for use inside a person's mouth.

In order to protect the teeth and other oral tissues of the user, it will be preferable for the carrier to have a pH in a range from about 5 to about 9, more preferably in a range from about 6 to about 8. Examples of buffers and bases that can be used to adjust the pH include citrate, citrate-bicarbonate, and phosphate buffers, sodium hydroxide and amines.

3. Thickening Agents

A common constituent within a carrier will be a thickening material, which may be used to provide bulk and a suitable consistency. Thickeners may be especially important in foamed dentifrice compositions since they may assist in stabilizing the entrained gas. They also may help keep the foamed composition firm and from having a liquid consistency. Hence, in a preferred embodiment, the foamed dentifrice compositions of the present invention will include a thickener as part of the carrier.

Appropriate thickeners may include either inorganic organic thickeners, or both. Inorganic thickeners that may be included in the dentifrice and toothpaste compositions of the present invention include fumed silicas dispersed in water, such as Cab-o-sil available from Cabot Corporation, and thickening silicas, including those available from W.R. Grace designated as Sylox 15.

Appropriate organic thickeners include natural and synthetic gums and colloids. Examples of organic thickeners include carrageenan (derived from Irish moss), xanthin gum, sodium carboxymethyl cellulose, starch, polyvinylpyrrolidone, hydroxyethylpropylcellulose, hydroxybutylmethylcellulose, hydroxypropylmethylcellulose, hydroxyethylcellulose, and carboxypolymethylene. Such materials are typically dispersed in water and/or other solvents, such as glycerine or polyethylene glycol.

Thickening materials will preferably be incorporated in the compositions of the is present invention in a concentration in a range from about 0.05% to about 25% by weight of the composition, and preferably in a range from about 0.1% to about 10% by weight.

4. Abrasives and Polishes

The carrier will typically include one or more abrasive materials to help clean and polish the teeth. Because solids are inexpensive and can add bulk, they will normally comprise a substantial fraction of the carrier. Almost any granular solid or powder can act as an abrasive or polish, although certain solids are preferred in order to clean, yet avoid scratching, the tooth enamel. Conventional abrasives typically include salts having anti-tartar activity and which include, but are not limited to, dicalcium orthophosphate, calcium carbonate, beta-phase calcium pyrophosphate, sodium metaphosphate, long chain polyphosphates such as sodium hexametaphosphate and cyclic phosphates such as sodium trimetaphosphate as well as alkylmetatripolyphosphates such as sodium tripolyphosphate and potassium tripolyphosphate.

Mixtures of abrasives can also be used. The total amount of abrasive in the dentifrice of the present invention will preferably be in a range from about 0.5% to about 95% by weight of the dentifrice, and more preferably in a range from about 20% to about 60% by weight of the dentifrice. The abrasive and polish components should be distinguished from the optional lightweight filler components since conventional abrasives and polishes usually have a density greater than about 1.5 $g/cm^3$. The term "abrasive" will include polishes, which are generally very fine abrasives.

Polishing agents may be included in dentifrice compositions that contain siliceous materials, such as silica, which have a mean particle size up to about 10 microns and a very high surface area, e.g. in the range of 150–750 square meters/gram. Polishing agents differ from abrasives mainly in the former having a smaller particle size. A preferred polishing agent is a precipitated amorphous hydrated silica, such as Sorbosil AC-35 marketed by Crosfield Chemicals. Other polishing agents may also be employed, including peroxide reactive polishing agents such as sodium bicarbonate, calcium carbonate, as well as sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, alumina trihydrate, aluminum silicate, zirconium silicate, calcined alumina, and bentonite.

When polishing agents are present in the dentifrice composition of the present invention, they are preferably included in a range from about 10% to about 30% by weight of the dental composition, more preferably in a range from about 5% to about 25% by weight.

5. Foaming and Stabilizing Agents

Foaming and stabilizing agents are typically included in prefoamed dental compositions, and aid in both entraining the gas to form the foam, and also assist in stabilizing the foam in many cases. As used in the present invention, the term "foaming agent" is defined as any substance that aids, or otherwise helps, the dentifrice composition become foamed or be maintained in a foamed state. Foaming agents generally work in conjunction with mechanical foaming devices, such as high speed mixing devices.

In order for pre-foamed dentifrice compositions to have a commercially practical shelf-life, the foamed compositions need to be shelf stable as a foam for prolonged periods of time and subsequently be ready for application. Stabilized foaming agents within the scope of the present invention should be non-toxic and should not contribute to the formation of carries. There are many foaming and stabilizing agents known that are capable of safely and effectively stabilizing foamed dentifrice compositions including, but are not limited to, soaps, proteins, extract of licorice root, fatty acids, and sulfite liquids.

6. Surfactants

Surfactants may be included in order to aid in dispersing the dentifrice composition throughout the oral cavity and also as a cleansing agent. They also may act as a foaming agent as discussed above. Surfactants help disperse the toothpaste within water and saliva found in the mouth during brushing. Surfactants may also improve the cosmetic acceptability and foaming properties of the dentifrice in the oral cavity.

Among the organic surfactants useful in the practice of the present invention are salts of the higher alkyl sulfates, such as sodium lauryl sulfate (SLS) or suitable alkyl sulfates having 8 to 18 carbon atoms in the alkyl group; sodium lauryl sulfoacetate, salts of sulfonated monoglycerides of higher fatty acids, such as sodium coconut monoglyceride, sulfonate or other suitable sulfonated monoglycerides of fatty acids of 10 to 18 carbons; salts of amides of high fatty acids, e.g., 12 to 16 carbon atoms, with lower aliphatic amino acids, such as sodium-N-methyl-N-palmitoyl taurides sodium N-lauroyl-, N-myristoyl- and N-palmitoyl sarcosinates; salts of esters of fatty acids with isothionic acid or with glycerol monosulfate, such as the sodium salt of monosulfated monoglyceride of hydrogenated coconut oil fatty acids; salts of olefin sulfonates, e.g, alkene sulfonates or hydroxyalkene sulfonates or mixtures thereof having 12 to 16 carbon atoms in the carbon chain of the molecule; and soaps of higher fatty acids, such as those of 12 to 18 carbon atoms, e.g., coconut fatty acids. The cation of the salt is typically sodium, potassium or mono-, di- or triethanolamine.

Mixtures of two or more surfactants can be used if desired to obtain desired properties. Additional useful surfactants may include the non-ionic, cationic, zwitterionic, amphoteric non-soap organic synthetic detergents. A full range of suitable surfactants is disclosed in U.S. Pat. No. 3,988,433 issued to Benedict, the disclosure of which has been incorporated herein by reference.

Surfactants are preferably included in the dentifrice of the present invention is at a concentration in a range from about 0.5% to about 3% by weight, and more preferably from about 1% to about 2% by weight.

7. Humectants

It may be desirable to include a humectant material in a dentifrice or toothpaste composition in order to maintain moisture in the composition and keep the composition from becoming excessively stiff or hardened. Suitable humectants include, but are not limited to glycerin, sorbitol, and other polyhydric alcohols that are suitable for human consumption. The humectant may be included in an amount up to about 40% by weight of the dentifrice composition. Alternatively, the dentifrice composition may contain up to about 40% by weight of a paraffin oil as a non-humectant softening agent.

8. Miscellaneous Components

Various other miscellaneous materials and components may be incorporated into the dentifrice composition of the present invention. Non-limiting examples of these various components include solid lightweight fillers, polishing agents, peroxides, colorants, dyes, flavoring and sweeteners.

Bicarbonate compounds, when included in the dentifrice components of the present invention as a cleansing or refreshening agent, are present at a concentration in a range from about 5% to about 20% by weight, and preferably in a range from about 8% to about 15% by weight. The particle size of the bicarbonate compounds can range from about 10 to about 300 microns. A particle size of about 20–60 microns is preferred, although the smaller particle size bicarbonate compounds can be more readily dispersed in the dentifrice carrier.

Peroxide compounds may be used as an ingredient in the dentifrice and toothpaste compositions of the present invention as a cleansing or whitening agent. When peroxide compounds are present in the dentifrice composition, the peroxide compounds are preferably included in a range from about 0.25% to about 5% by weight of the dentifrice composition, more preferably in a range from about 0.5% to about 2.0% by weight. Peroxide compounds suitable for use with the dentifrice and toothpaste compositions of the present invention include metal peroxides such as calcium peroxide, magnesium peroxide, and zinc peroxide.

Colorants such as pigments and dyes may be used in the practice of the present invention. Pigments include non-toxic, water insoluble inorganic pigments such as titanium dioxide and chromium oxide greens, ultramarine blues and pinks and ferric oxides, as well as water insoluble dye lakes prepared by extending calcium or aluminum salts of FD&C dyes on alumina such as FD&C Green #1 lake, FD&C Blue #2 lake, FD&C #30 lake and FD&C # Yellow 15 lake. The pigments have a particle size in a range of about 0. 1–500 microns, preferably about 0.1–50 microns, and are preferably included in a concentration of about 0.5% to about 3% by weight.

Dyes used in the practice of the present invention are generally food color additives presently certified under the Food Drug and Cosmetic Act for use in food and ingested drugs, including dyes such as FD&C Yellow No. 5 (sodium salt of 4-p-sulfophenylazo-1-p-sulfophenyl-5-hydroxypyrazole-3 carboxylic acid), FD&C Yellow No. 6 (sodium salt of p-sulfophenylazo-B-naphthol-6-monosulfonate), FD&C Green No. 3 (disodium salt of 4-{4-(N-ethyl-p-sulfobenzylamino)-phenyl]-(4-hydroxy-2-sulfoniumphenyl) methylene}-[1-(N-ethyl-N-p-sulfobenzyl)-δ-3, 5-cyclohexadienimine], FD&C Blue No. 1 (disodium salt of dibenzyldiethyldiaminotriphenylcarbinol trisulfonic acid anhydride), FD&C Blue No. 2 (sodium salt of disulfonic acid of indigotin) and mixtures thereof in various proportions. The preferred concentration of dye for the most effective result, when dyes are used in the present invention, is in an amount in a range from about 0.05% to about 10% by weight of the dentifrice compositions, and preferably from about 0.5% to about 2% of the total weight of the dentifrice composition.

Any suitable flavoring or sweetening material may also be incorporated in the dentifrice composition of the present invention. Examples of suitable flavoring constituents are flavoring oils, e.g., oils of spearmint, peppermint, wintergreen, sassafras, clove, sage, eucalyptus, marjoram, cinnamon, lemon, orange, and methyl salicylate. Suitable sweetening agents include sucrose, lactose, maltose, sorbitol, sodium cyclamate, perillartine, and sodium saccharin. Suitable flavor and sweetening agents may together comprise from about 0.01% to about 5% of the dentifrice compositions.

Various other materials may be incorporated into the dentifrice composition of this invention. Non-limiting examples thereof include preservatives, silicones and chlorophyll compounds, antibacterial agents such as chlorohexadene, halogenated diphenyl ethers such as Triclosan, desensitizing agents such as potassium nitrate and potassium citrate and mixtures thereof. These adjuvants are incorporated in the dentifrice composition in amounts which do not substantially adversely affect the properties and characteristics desired, and are selected and used in proper amounts, depending upon the particular type of dentifrice component involved.

B. Density-Reducing Means

The terms "density-reducing means" and "density-reducing component" shall include entrained gas and/or lightweight filler components. In general, the density reducing means shall comprise the constituent that is primarily added to the base composition in order to reduce the density and increase the bulk and volume of the final dental composition. It should be understood that reducing the density is the same as increasing the volume and bulk per unit weight. In this way, the volume of the dental composition can be significantly or greatly increased by the density reducing means in order to allow a larger volume of the dental composition to be introduced onto a toothbrush, while reducing the actual amount of fluoride and other active ingredients actually delivered into a person's mouth compared to the base composition.

In a preferred embodiment, the density reducing means will comprise entrained air or other gas. Entraining gas yields a final composition in which the final concentration of the fluoride or other active ingredient remains essentially the same as before the gas was added to the base composition. Moreover, gases are versatile because they may be readily entrained within dental compositions during manufacture or in situ at the time of use. Gases also tend to be inert and nonreactive vis-a-vis the active ingredients.

In conjunction with, or at least partially in lieu of, the entrained gas, the density reducing means may include a solid, lightweight filler. The solid lightweight filler can be used to greatly decrease the density of the inventive dental compositions and provide lightweight bulk therein. A solid lightweight filler is defined as a material having a relatively low density or specific gravity typically less than about 1 $g/cm^3$, preferably less than about 0.50 $g/cm^3$, more preferably less than about 0.3 $g/cm^3$, and most preferably less than about 0.1 $g/cm^3$. Because lightweight fillers can act to displace a substantial portion of the active dentifrice without substantially reducing the weight percent of the active dental agent, lightweight solids can behave similarly to entrained gas, as described herein.

Solid, low density fillers may be organic or inorganic. Examples of lightweight inorganic fillers include perlite, vermiculite, hollow glass spheres, lightweight expanded geologic materials, polypropylene particles, and the like. Examples of lightweight organic fillers include cork, polystyrene foam particles, polypropylene particles, and other expanded polymeric materials.

In addition to greatly reducing the density of the dental composition, solid lightweight fillers can also impart some abrasive action in addition to the abrasive or polishing components added to the dental compositions. Although any lightweight filler may be useful in reducing the density of the inventive dental compositions, the lightweight fillers should be selected to be safe when placed within the oral cavity of a human.

III. PREPARATION OF THE INVENTIVE DENTAL COMPOSITIONS

The dentifrice and toothpaste compositions which are foamed to form the foamed dentifrice and toothpaste compositions of the present invention are prepared using conventional techniques known in the art. For example, the dentifrice or toothpaste compositions can be prepared by blending each of the solid ingredients into a liquid carrier component, i.e., polyalkylene glycol, which is normally viscous at room temperature. Conventional adjuvants can then be included.

Once the desired dentifrice or toothpaste composition is formed, the composition is foamed to form a foamed dentifrice or toothpaste composition within the scope of the present invention. Foam is produced in dentifrice or toothpaste compositions by introducing air or a gas into the toothpaste or dentifrice composition. Examples of foaming dentifrice or toothpaste compositions include foaming by mechanical means or chemical means. Alternatively, gas can be incorporated into the dental composition, which is then stored in compressed form under pressure. Upon dispensing the composition, the compressed gas will develop foam within the toothpaste upon being exposed to atmospheric pressure.

In one embodiment, the dentifrice composition is foamed prior to packaging (referred to as pre-foamed). When the dentifrice composition is foamed and then packaged, the dentifrice composition preferably comprises a foam stabilizing agent so that the foamed dentifrice composition is shelf-stable for a commercially practical period of time. The dentifrice composition is preferably foamed using mechanical means, such as high speed mixing or other agitation. The foamed composition is then placed into a suitable container, such as a conventional toothpaste tube or pump container for storage. The inventive compositions should be stable as a foam: i) after mixing; ii) after storage of the composition for extended periods of time; and iii) after delivering a portion of the foamed composition from the container. Hence, upon opening and using a portion of the foamed toothpaste, the remaining foamed toothpaste can be resealed and reused while remaining as a stable foamed composition.

In another embodiment of the present invention, chemical foaming agents are used to foam the dentifrice composition prior to packaging. Chemical foaming agents create foam or entrained gas when the foaming chemicals are mixed together. An example of chemical foaming is the formation of carbon dioxide from the chemical reaction of aluminum sulfate and sodium bicarbonate. As with mechanical foaming, a foam stabilizer is preferably included with the chemically foamed dentifrice compositions in order to stabilize the foamed composition during storage, use and reuse.

In still another embodiment, the dentifrice composition may constitute a pressurized foaming composition. As used in the present invention, the term "pressurized foaming composition" is defined as a suspension of compressed gas voids within a liquid. A common example of a pressurized foaming composition is conventional shaving cream, wherein a gas is compressed in a container and upon release, a foamed material is produced. In connection with the present invention, the dentifrice composition is formed using conventional methods as discussed above. The dentifrice composition is then placed in a container with a suitable compressed gas, under pressure, using conventional compression techniques known in the art. Subsequently, when the dentifrice composition is dispensed from the container, the pressure of the gas causes the dentifrice composition to be dispensed as a foamed dentifrice composition. An example of a suitable propellant and foaming agent is carbon dioxide gas. Alternatively, the dentifrices can be placed into a container under pressure along with foaming agents that will cause the dentifrice to foam upon being dispensed from the container and being exposed to the atmosphere. Similarly, a container of toothpaste can be provided in conjunction with a separate compartment of compressed gas, which gas can mix with the toothpaste during the dispensing process in order to foam the toothpaste at the time of use.

In yet another embodiment, air can be entrained into the initially unfoamed dental composition by means of the pumping action required to express the dental composition from the container within which it is stored.

IV. CHARACTERISTICS OF THE INVENTIVE DENTAL COMPOSITIONS

In order for the inventive foam dental compositions to behave and seem like conventional toothpaste, the carrier should have a viscosity such that when substantial quantities of air and/or lightweight aggregates are entrained or mixed therein, the toothpaste will have a viscosity, yield stress, and other rheological properties such that it will flow from the storage container onto the toothbrush and substantially maintain itself as a bead or line of composition across the tooth bristles for at least a short period of time. If the composition is too runny or nonviscous, the foam might collapse such that material could fall between the bristles of the toothbrush and cause the user to use more of the composition than is intended. On the other hand, the material should not be so stiff and viscous that it cannot be easily expressed from the container without undue difficulty. In light of the disclosure set forth herein, one of ordinary skill in the art will know how to adjust the various components within the carrier material in order to obtain a stiffness and viscosity that will satisfy the aforementioned criteria.

Once the dental composition has been foamed, either during mixing to form a pre-foamed dental composition or in situ using compressed gas, the dental composition will include entrained gas or air in a range from about 10% and about 90% by volume of the foamed composition, preferably greater than about 20% by volume, more preferably greater than about 30% by volume, and most preferably greater than about 50% by volume of the foamed toothpaste or dentifrice composition.

The foregoing concentrations of gas or air are measured at the time the dental composition is dispensed from the storage container onto a toothbrush or other applicator means. However, they do not constitute a limitation as to when foaming or expansion of the dental composition actually occurs. Though it might be said that the dental composition has a certain concentration of entrained gas "upon dispensing the dental composition from a storage container", it will be appreciated that the dental composition may either be pre-foamed or foamed in situ using, e.g., compressed gas.

In the event that a lightweight filler material is used in conjunction with, or in place of, entrained gas or air in order to reduce the density of the dental composition, the amount of lightweight filler will be such so as to maintain an appropriate rheology as described above. Moreover, the weight of the lightweight filler should be factored into the overall weight of the composition when determining the weight percent of the active dental agent. It may thus be necessary to increase the amount of the active ingredients by some degree to maintain the desired concentration due to the weight increasing effect of the lightweight filler.

In order to achieve the benefits of the present invention, the lightweight filler material will be included within the composition, if included at all, in an amount such that the dental composition has a reduction in density in a range from about 10% to about 90% compared to the density of the initial composition exclusive of the lightweight filler material. Preferably, the reduction in density will be greater than about 20% in comparison to the initial dental composition exclusive of the lightweight filler. More preferably, the reduction in density will be greater than about 30% and, most preferably, greater than about 50% in comparison to the initial dental composition exclusive of the lightweight filler. Either entrained air and/or lightweight filler will comprise means for reducing the density of the dental composition.

As can be seen, the reduction in density caused by the lightweight filler, alone or in combination with entrained air, corresponds to the preferred ranges of the volume of entrained air within foamed dental compositions that do not include lightweight fillers. As such, when both entrained gas and lightweight filler material are incorporated, it can readily be seen that the preferred reduction in the density of the dental composition will be approximately the same as where it is reduced simply by incorporating gas or air, which contributes no mass while contributing high volume. This is also true for where a lightweight aggregate is used exclusively to reduce the density of the composition.

Because there is a direct correlation between the reduction of density and the increase of the bulk and volume of the dental composition per unit weight, it may be helpful to understand how the reduction in density increases the volume of the dental compositions according to the invention. A 10% decrease in the density of the base composition roughly translates into an increase in the volume per unit weight of about 11%, meaning that the final dental composition has a volume that is 111% of the initial volume of the base composition. On the other hand, reducing the density by 90% translates into an increase in the volume per unit weight of 900%, which means that the final dental composition has a volume that is 1000% of the base composition. Likewise, a 20% decrease in the density constitutes a 25% increase of the initial volume such that the final volume of 125% of the initial volume of the base composition; a 30% decrease in the density translates into a volume increase of about 43%; a 50% decrease in the density translates into a doubling of the volume, or an increase of 100%; and a decrease in density of 66.7% translates into a tripling of the volume, or an increase of 300%, which means that the final dental composition has 400% of the volume of the base composition, or 4 times the volume.

V. EXAMPLES OF THE PREFERRED EMBODIMENTS

The following examples are presented in order to more specifically teach the preferred compositions and methods for forming and using carbonaceous agglomerates according to the present invention. Although the examples are hypothetical in nature, they are based on or derived from actual mix designs and conditions for making lower density dental compositions according to the present invention.

Example 1

Dental compositions suitable for use in brushing or cleaning teeth are made from a base composition having the following components, exclusive of density reduction means, expressed as a percentage by weight of the base composition exclusive of the density reduction means:

| | |
|---|---|
| Distilled water | 30% |
| Glycerin | 25% |
| Flavor and color | 1.5% |
| Mannitol | 15% |
| Sodium laurel sulfate | 2% |
| Xanthan gum | 1% |
| Abrasive silicon dioxide | 25% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 10–90% in 5% increments. By way of example, if 10% by volume of a gas is entrained within the base composition, the resulting composition will have a density that is essentially 90% of the density of the base composition, or a density reduction of essentially 10% compared to the base composition. Increasing the volume of gas that is entrained reduces the density of the resulting composition by a corresponding amount. Entraining 90% by volume air will reduce the density by 90%, resulting in a final composition having 10% of the density of the base composition. In addition, because the mass of the entrained gas is negligible, the concentration of fluoride remains essentially the same in all cases.

In the case where some or all of the density reduction means comprises a low density filler, there will not be a 1:1 reduction in density as more low density of filler is added. However, the reduction of density is still substantial, even dramatic, so long as the density of the filler is substantially less than the density of the base composition. However, slight adjustments in the fluoride content may be necessary to maintain the desired fluoride concentration in the final dental compositions.

As discussed above, assuming that a "pea-size" amount is ⅓ the "normal amount", then it would be necessary to include enough density reduction means to reduce the density of the base composition by ⅔ to yield a final composition having only ⅓ the density of the base composition. In this way, one can use three times of the reduced density composition compared to the base composition and still put the same amount of fluoride into his or her mouth. Thus, an amount of reduced density toothpaste sufficient to cover an entire adult toothbrush (as depicted in FIG. 3) will, in reality, be equivalent to using a pea-size amount of the base composition (as depicted in FIG. 2).

However, because a child-sized toothbrush is roughly 50% the size of an adult toothbrush, the final dental composition only needs to have a density reduction of ⅓. In other words, because the volume of toothpaste required to totally cover the bristles of a child-sized toothbrush is about 50% of the volume required to cover an adult toothbrush, a "pea-size" amount is roughly ⅔ of the volume needed to cover a child-size toothbrush. Thus, assuming that a child will want to cover the bristles of a child-size toothbrush with toothpaste, a reduced-density dental composition would only need to have a density reduction of about ⅓ in order for the toothbrush-covering amount to be equivalent to the recommended pea-size amount.

Example 2

Dental compositions suitable for use in brushing or cleaning teeth are made from a base composition having the following components, exclusive of density reduction means, expressed as a percentage by weight of the base composition exclusive of the density reduction means:

| | |
|---|---|
| Distilled Water | 20% |
| Propylene glycol | 35% |
| Flavor and color | 1.5% |
| Sorbitol | 15% |
| Potassium laurate | 1% |
| Polysorbate 60 | 1% |
| Carbomer 974 NF | 1% |
| Abrasive aluminum oxide | 25% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 10–90% in 5% increments. The density reduction means may comprise both gases and low density solids as discussed herein. The remaining discussion of Example 1 is incorporated herein by reference.

Example 3

Dental compositions suitable for use in brushing or cleaning teeth are made from a base composition having the following components, exclusive of density reduction means, expressed as a percentage by weight of the base composition exclusive of the density reduction means:

| | |
|---|---|
| Distilled Water | 20% |
| Propylene glycol | 20% |
| Polyethylene glycol 300 | 15% |
| Flavor and color | 1.5% |
| Xylitol | 15% |
| Octaoxyethlylene glycol monododecyl ether | 1% |
| Polysorbate 20 | 1% |
| Pemulen TR-1 NF | 2% |
| Abrasive aluminum oxide | 25% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 10–90% in 5% increments. The density reduction means may comprise both gases and low density solids as discussed herein. The remaining discussion of Example 1 is incorporated herein by reference.

Example 4

Dental compositions suitable for use in brushing or cleaning teeth are made from a base composition having the following components, exclusive of density reduction means, expressed as a percentage by weight of the base composition exclusive of the density reduction means:

| | |
|---|---|
| Glycerin | 31% |
| Polyethylene glycol 300 | 35% |
| Flavor and color | 1.5% |
| Sodium saccharin | 1% |
| Potassium laurate | 1% |
| Polyalkylene oxide modified polydimethyl siloxanes | 1% |
| Sodium oleate | 2% |

| Fumed Silicon dioxide | 2% |
|---|---|
| Abrasive calcium fluorosilicate | 25% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 10–90% in 5% increments. The density reduction means may comprise both gases and low density solids as discussed herein. The remaining discussion of Example 1 is incorporated herein by reference.

Example 5

Dental compositions suitable for use in brushing or cleaning teeth are made from a base composition having the following components, exclusive of density reduction means, expressed as a percentage by weight of the base composition exclusive of the density reduction means:

| Distilled Water | 57% |
|---|---|
| Flavor and color | 1.5% |
| Phenylalanine | 1% |
| Sodium decane sulfonate | 1% |
| Carbomer 934 | 4% |
| Abrasive aluminum oxide | 25% |
| Hollow silicon dioxide spheres | 10% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 10–90% in 5% increments. The density reduction means may comprise both gases and low density solids as discussed herein. The remaining discussion of Example 1 is incorporated herein by reference.

Example 6

Dental compositions suitable for use in brushing or cleaning teeth are made from a base composition having the following components, exclusive of density reduction means, expressed as a percentage by weight of the base composition exclusive of the density reduction means:

| Distilled Water | 20% |
|---|---|
| Propylene glycol | 35% |
| Flavor and color | 1.5% |
| Mannose | 15% |
| Tetradecyltrimethyl ammonium bromide | 1% |
| Sodium di-2-ethylhexyl sulfosuccinate | 1% |
| Locust bean gum | 1% |
| Abrasive titanium dioxide | 22% |
| Hollow aluminum oxide spheres | 3% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 10–90% in 5% increments. The density reduction means may comprise both gases and low density solids as discussed herein. The remaining discussion of Example 1 is incorporated herein by reference.

Example 7

Dental compositions suitable for use in brushing or cleaning teeth are made from a base composition having the following components, exclusive of density reduction means, expressed as a percentage by weight of the base composition exclusive of the density reduction means:

| Propylene glycol | 55% |
|---|---|
| Flavor and color | 1.5% |
| Fructose | 15% |
| Carbomer 910 | 3% |
| Abrasive mica | 22% |
| Hollow silicon dioxide spheres | 5% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 10–90% in 5% increments. The density reduction means may comprise both gases and low density solids as discussed herein. The remaining discussion of Example 1 is incorporated herein by reference.

Example 8

Dental compositions suitable for use in brushing or cleaning teeth are made from a base composition having the following components, exclusive of density reduction means, expressed as a percentage by weight of the base composition exclusive of the density reduction means:

| Distilled Water | 20% |
|---|---|
| Polyethylene glycol | 35% |
| Flavor and color | 1.5% |
| Sorbitol | 15% |
| Abrasive silicon dioxide | 20% |
| Mica | 8% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 10–90% in 5% increments. The density reduction means may comprise both gases and low density solids as discussed herein. The remaining discussion of Example 1 is incorporated herein by reference.

Example 9

Dental compositions suitable for use in brushing or cleaning teeth are made from a base composition having the following components, exclusive of density reduction means, expressed as a percentage by weight of the base composition exclusive of the density reduction means:

| Distilled Water | 20% |
|---|---|
| Glycerin | 50% |
| Flavor and color | 1.5% |
| Sucralose | 1% |

| | |
|---|---|
| Sodium deoxycholate | 2% |
| Abrasive aluminum oxide | 20% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 10–90% in 5% increments. The density reduction means may comprise both gases and low density solids as discussed herein. The remaining discussion of Example 1 is incorporated herein by reference.

Example 8

Dental compositions suitable for use in brushing or cleaning teeth are made from a base composition having the following components, exclusive of density reduction means, expressed as a percentage by weight of the base composition exclusive of the density reduction means:

| | |
|---|---|
| Distilled Water | 20% |
| Polyethylene glycol | 35% |
| Flavor and color | 1.5% |
| Sorbitol | 15% |
| Abrasive silicon dioxide | 20% |
| Perlite | 8% |
| Fluoride source and preservative | 0.5% |

The dental compositions made according to this example include density reduction means dispersed throughout the base composition in various amounts. The final dental compositions include various quantities of density reduction means in order for the density of the base composition to be reduced by 10–90% in 5% increments. The density reduction means may comprise both gases and low density solids as discussed herein. The remaining discussion of Example 1 is incorporated herein by reference.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. In the fluoride delivering dental method for a child, one having the tendency to apply too much fluoride toothpaste onto its child-sized toothbrush, to lay out a solid strip of fluoride toothpaste across the length of the tops of the bristles of its child-sized toothbrush, as adults do on the entire length of their adult-sized toothbrush, instead of a pea-sized quantity laid on the child's toothbrush, said pea-sized amount being typically about ⅓ the amount of toothpaste needed to fully cover the tops of the bristles an adult-sized toothbrush, whereby the ingestion of too much fluoride can lead to the development of fluorosis, causing brown mottled enamel, said fluoride toothpaste having a quantity of fluoride that while safe when ingested by an adult might be harmful if ingested by a child, said toothpaste tasting good to encourage brushing, said good taste having the negative side effect of enticing children to swallow the toothpaste while they brush, the taste having a tendency to cause children to swallow substantial amounts of fluoride toothpaste, the improvement comprising the steps of:

(1) providing an expanded dental composition which comprises:
  (a) a base composition including a fluoride source, an abrasive solid, and a carrier selected from the group consisting of liquids, gels, and mixtures thereof; and
  (b) a gaseous component dispersed throughout the base composition and included in an amount in order to increase the volume of the base composition so as to yield the expanded dental composition, the expanded dental composition having a volume in relation to the base composition so that an amount of the expanded dental composition sufficient to substantially cover the tops of the bristles of a child-sized toothbrush provides a quantity of fluoride that does not significantly exceed the quantity of fluoride that would be provided by a pea-size quantity of the base composition absent the gaseous component; and (2) contacting a child's teeth with the expanded dental composition.

2. A method as defined in claim 1, wherein the gaseous component reduces the density of the expanded dental composition by an amount greater than about 20% in relation to the density the base composition.

3. A method as defined in claim 1, wherein the gaseous component reduces the density of the expanded dental composition by an amount greater than about 30% in relation to the density the base composition.

4. A method as defined in claim 1, wherein the gaseous component reduces the density of the expanded dental composition by an amount greater than about 50% in relation to the density the base composition.

5. A method as defined in claim 1, wherein the gaseous component comprises a gas that is dispersed throughout the base composition during manufacture such that the expanded dental composition comprises a pre-foamed dental composition.

6. A method as defined 5, wherein the gas is included within the expanded dental composition in an amount in a range from about 10% to about 90% by volume of the expanded dental composition.

7. A method as defined in claim 5, wherein the expanded dental composition further includes a foaming agent that stabilizes the pre-foamed dental composition such that the expanded dental composition is capable of being stored for a desired period of time within a storage container without significant collapse of the foam.

8. A method as defined in claim 1, wherein the expanded dental composition further includes a lower density solid filler that, in combination with the gaseous component, yields a desired level of expansion.

9. A method as defined in claim 1, wherein the gaseous component comprises initially compressed gas that causes the base composition to foam and expand to form the expanded dental composition upon dispensing the base composition and compressed gas from a storage container.

10. A method as defined in claim 9, wherein the compressed gas is premixed with the base composition and the premixed compressed gas and base composition are initially stored within a pressurized storage container.

11. A method as defined in claim 9, wherein the compressed gas is stored in a compartment separate from, but in communication with, a storage container containing the base composition such that the compressed gas mixes with the base composition and causes the base composition to foam and expand upon dispensing the mixture of base composition and compressed gas.

12. A method as defined in claim 1, wherein the fluoride source is included in an amount such that the expanded dental composition provides a fluoride ion concentration in a range from about 10 ppm to about 3500 ppm.

13. A method as defined in claim 1, wherein the fluoride ion source is included in an amount such that the expanded dental composition provides a fluoride ion concentration in a range from about 850 ppm to about 1150 ppm.

14. A method as defined in claim 1, wherein the expanded dental composition has a volume in a range from about 110% to about 1000% relative to the volume of the base composition absent the gaseous component.

15. A method as defined in claim 14, wherein the expanded dental composition has a volume greater than about 125% relative to the volume of the base composition absent the gaseous component.

16. A method as defined in claim 14, wherein the expanded dental composition has a volume greater than about 200% relative to the volume of the base composition absent the gaseous component.

17. A method as defined in claim 14, wherein the expanded dental composition has a volume greater than about 400% relative to the volume of the base composition absent the gaseous component.

18. In the fluoride delivering dental method for a child, one having the tendency to apply too much fluoride toothpaste onto its child-sized toothbrush, to lay out a solid strip of fluoride toothpaste across the length of the tops of the bristles of its child-sized toothbrush, as adults do on the entire length of their adult-sized toothbrush, instead of a pea-sized quantity laid on the child's toothbrush, said pea-sized amount being typically about 1/3 the amount of toothpaste needed to fully cover the tops of the bristles an adult-sized toothbrush, whereby the ingestion of too much fluoride can lead to the development of fluorosis, causing brown mottled enamel, said fluoride toothpaste having a quantity of fluoride that while safe when ingested by an adult might be harmful if ingested by a child, said toothpaste tasting good to encourage brushing, said good taste having the negative side effect of enticing children to swallow the toothpaste while they brush, the taste having a tendency to cause children to swallow substantial amounts of fluoride toothpaste, wherein the improvement comprises the steps of:

(1) providing a pre-foamed dental composition comprising:

(a) a base composition including a fluoride source, an abrasive solid, and a carrier selected from the group consisting of liquids, gels, and mixtures thereof; and (b) entrained gas dispersed throughout the base composition in an amount in a range from about 10% to about 90% by volume of the pre-foamed dental composition such that the entrained gas increases the volume of the pre-foamed dental composition by an amount in a range from about 110% to about 1000% relative to the volume of the base composition exclusive of the volume of the entrained gas, wherein an amount of the pre-foamed dental composition sufficient to substantially cover the tops of the bristles of a child-sized toothbrush provides a quantity of fluoride that does not significantly exceed the quantity of fluoride that would be provided by a pea-size quantity of the base composition absent the entrained gas; and (2) contacting a child's teeth with the pre-foamed dental composition.

19. A method as defined in claim 18, wherein the entrained gas has a concentration greater than about 20% by volume of the pre-foamed dental composition upon delivering the pre-foamed dental composition from a storage container.

20. A method as defined in claim 18, wherein the entrained gas has a concentration greater than about 30% by volume of the pre-foamed dental composition upon delivering the pre-foamed dental composition from a storage container.

21. A method as defined in claim 18, wherein the entrained gas has a concentration greater than about 50% by volume of the pre-foamed dental composition upon delivering the pre-foamed dental composition from a storage container.

22. A method as defined in claim 18, wherein the pre-foamed dental composition undergoes further expansion in situ upon dispensing the pre-foamed dental composition from a storage container.

23. A method as defined in claim 18, wherein the pre-foamed dental composition further includes a lower density solid filler.

24. A method as defined in claim 18, wherein the fluoride source is included in an amount such that the pre-foamed dental composition provides a fluoride ion concentration in a range from about 10 ppm to about 3500 ppm.

25. A method as defined in claim 18, wherein the fluoride source is included in an amount such that the pre-foamed dental composition provides a fluoride ion concentration in a range from about 850 ppm to about 1150 ppm.

26. A method as defined in claim 18, wherein the fluoride source is included in an amount such that the pre-foamed dental composition provides a fluoride ion concentration of about 900 ppm.

27. A method as defined in claim 18, the pre-foamed dental composition further including an antimicrobial agent.

28. A method as defined in claim 18, the pre-foamed dental composition further including a desensitizing agent.

29. In the fluoride delivering dental method for a child, one having the tendency to apply too much fluoride toothpaste onto its child-sized toothbrush, to lay out a solid strip of fluoride toothpaste across the length of the tops of the bristles of its child-sized toothbrush, as adults do on the entire length of their adult-sized toothbrush, instead of a pea-sized quantity laid on the child's toothbrush, said pea-sized amount being typically about 1/3 the amount of toothpaste needed to fully cover the tops of the bristles an adult-sized toothbrush, whereby the ingestion of too much fluoride can lead to the development of fluorosis, causing brown mottled enamel, said fluoride toothpaste having a quantity of fluoride that while safe when ingested by an adult might be harmful if ingested by a child, said toothpaste tasting good to encourage brushing, said good taste having the negative side effect of enticing children to swallow the toothpaste while they brush, the taste having a tendency to cause children to swallow substantial amounts of fluoride toothpaste, wherein the improvement comprises the steps of:

(1) providing an expanded dental composition comprising:

(a) a base composition including a fluoride source, an abrasive solid, and a carrier selected from the group consisting of liquids, gels, and mixtures thereof; and (b) a gaseous component and a lower density solid filler component which are dispersed throughout the base composition and included in amounts sufficient to increase the volume of the base composition so as to yield the expanded dental composition, the expanded dental composition having a volume in relation to the base composition so that an amount of the expanded dental composition sufficient to substantially cover the tops of the bristles of a child-sized toothbrush provides a quantity of fluoride that does not significantly exceed the quantity of fluoride that would be provided by a pea-size quantity of the base composition absent the gaseous and lower density solid filler components; and (2) contacting a child's teeth with the expanded dental composition.

30. A method as defined in claim 29, wherein the lower density solid filler component is included in an amount so as to increase the volume of the expanded dental composition by an amount greater than about 20% in relation to the volume of the base composition absent the lower density solid filler component.

31. A method as defined in claim 29, wherein the lower density solid filler component is included in an amount so as to increase the volume of the expanded dental composition by an amount greater than about 30% in relation to the volume of the base composition absent the lower density solid filler component.

32. A method as defined in claim 29, wherein the lower density solid filler component is included in an amount so as to increase the volume of the expanded dental composition by an amount greater than about 50% in relation to the volume of the base composition absent the lower density solid filler component.

33. A method as defined in claim 29, wherein the lower density solid filler component has a density less than about 0.5 g/cm$^3$.

34. A method as defined in claim 29, wherein the lower density solid filler component has a density less than about 0.3 g/cm$^3$.

35. A method as defined in claim 29, wherein the lower density solid filler component has a density less than about 0.1 g/cm$^3$.

36. A method as defined in claim 29, wherein the lower density solid filler component imparts an abrasive action to the expanded dental composition.

37. A method as defined in claim 29, wherein the lower density solid filler component comprises an inorganic material.

38. A method as defined in claim 1, wherein the step of contacting a child's teeth with the expanded dental composition is performed using a child-sized toothbrush.

39. A method as defined in claim 1, wherein the step of contacting a child's teeth with the expanded dental composition is performed using an adult-sized toothbrush.

40. A method as defined in claim 18, wherein the step of contacting a child's teeth with the pre-foamed dental composition is performed using a child-sized toothbrush.

41. A method as defined in claim 18, wherein the step of contacting a child's teeth with the pre-foamed dental composition is performed using an adult-sized toothbrush.

42. A method as defined in claim 29, wherein the step of contacting a child's teeth with the expanded dental composition is performed using a child-sized toothbrush.

43. A method as defined in claim 29, wherein the step of contacting a child's teeth with the expanded dental composition is performed using an adult-sized toothbrush.

* * * * *

UNITED STATES PATENT AND TRADEMARK OFFICE
CERTIFICATE OF CORRECTION

PATENT NO. : 6,010,683
DATED : January 4, 2000
INVENTOR(S) : Dan E. Fischer

It is certified that error appears in the above-identified patent and that said Letters Patent are hereby corrected as shown below:

Col. 2, ln. 2: after "developed" change "toothpaste" to --toothpastes--

Col. 2, ln. 7: after "tentionally" change "shallow" to --swallow--

Col. 5, ln. 23: before "discomfort" change "trointestinal" to --tro-intestinal--

Col. 6, ln. 13: after "manufacturing" and before "and" insert --toothpastes--

Col. 7, ln. 41: after "including" change "lessor" to --lesser--

Col. 7, ln. 52: after "average" change "ingestfar" to --ingest far--

Col. 11, ln. 51: after "inorganic" insert --,or--

Col. 12, ln. 2: after "of the" and before "present" delete [is]

Col. 13, ln. 44: after "invention" and before "at a " delete [is]

Col. 14, ln. 27: after "FD&C" change "# Yellow" to --Yellow #--

Col. 23, ln. 16: after "Example" change "8" to --10--

Col. 23, ln. 59: after "bristles" and before "an" insert --of--

Col. 24, ln. 24: after "density" and before "the base" insert --of--

Col. 24, ln. 28: after "density" and before "the base" insert --of--

UNITED STATES PATENT AND TRADEMARK OFFICE
CERTIFICATE OF CORRECTION

Page 2 of 2

PATENT NO. : 6,010,683
DATED : January 4, 2000
INVENTOR(S) : Dan E. Fischer

It is certified that error appears in the above-identified patent and that said Letters Patent are hereby corrected as shown below:

Col. 24, ln. 32: after "density" and before "the base" insert --of--

Col. 24, ln. 38: after "defined" and before "5," insert --in claim--

Col. 25, ln. 32: after "bristles" and before "an" insert --of--

Col. 26, ln. 45: after "bristles" and before "an" insert --of--

Signed and Sealed this

Fifteenth Day of May, 2001

Attest:

NICHOLAS P. GODICI

Attesting Officer    Acting Director of the United States Patent and Trademark Office